United States Patent
Aharonov et al.

(10) Patent No.: US 10,906,953 B2
(45) Date of Patent: Feb. 2, 2021

(54) METHODS OF PURIFICATION AND/OR VIRAL INACTIVATION

(71) Applicant: FERRING B.V., Hoofddorp (NL)

(72) Inventors: Jenny Aharonov, Hoofddorp (NL); Elinor Erez, Hoofddorp (NL); Eli Harosh, Hoofddorp (NL)

(73) Assignee: FERRING B.V., Hoofddorp (NL)

( * ) Notice: Subject to any disclaimer, the term of this patent is extended or adjusted under 35 U.S.C. 154(b) by 48 days.

(21) Appl. No.: 15/737,524

(22) PCT Filed: Jun. 24, 2016

(86) PCT No.: PCT/EP2016/064668
§ 371 (c)(1),
(2) Date: Dec. 18, 2017

(87) PCT Pub. No.: WO2016/207353
PCT Pub. Date: Dec. 29, 2016

(65) Prior Publication Data
US 2019/0002518 A1   Jan. 3, 2019

(30) Foreign Application Priority Data
Jun. 26, 2015   (EP) .................................... 15174029

(51) Int. Cl.
| | |
|---|---|
| *C07K 14/59* | (2006.01) |
| *C07K 1/30* | (2006.01) |
| *B01D 15/32* | (2006.01) |
| *B01D 15/36* | (2006.01) |
| *B01D 21/00* | (2006.01) |
| *B01D 39/20* | (2006.01) |
| *B01D 61/14* | (2006.01) |
| *A61K 38/00* | (2006.01) |

(52) U.S. Cl.
CPC ............ *C07K 14/59* (2013.01); *B01D 15/327* (2013.01); *B01D 15/362* (2013.01); *B01D 15/363* (2013.01); *B01D 21/00* (2013.01); *B01D 39/2017* (2013.01); *B01D 61/145* (2013.01); *C07K 1/30* (2013.01); *A61K 38/00* (2013.01)

(58) Field of Classification Search
None
See application file for complete search history.

(56) References Cited

U.S. PATENT DOCUMENTS 4,939,176 A   7/1990   Seng et al.

FOREIGN PATENT DOCUMENTS

| CN | 103275206 B | | 9/2014 | |
|---|---|---|---|---|
| EP | 0 201 390 B1 | | 12/1986 | |
| EP | 0374625 | * | 6/1990 | ............... A61L 2/18 |
| EP | 0 452 753 A1 | | 10/1991 | |
| EP | 2 719 704 A1 | | 4/2014 | |
| FR | 1311764 A | | 12/1962 | |
| RU | 2370500 C2 | | 10/2009 | |
| WO | WO-00/56768 A2 | | 9/2000 | |
| WO | WO-2009/127826 A1 | | 10/2009 | |
| WO | WO-2010/034198 A1 | | 4/2010 | |
| WO | WO-2015/056237 | | 4/2015 | |
| WO | WO-2011/042688 A1 | | 10/2016 | |

OTHER PUBLICATIONS

Dichtelmüller et al., Biologicals, 2002; 30: 135-142 (Year: 2002).*
Kandula et al., Biotechnol. Appl. Biochem., 2009; 54, 149-155 (Year: 2009).*
Zheng et al., mAbs 3:6, 568-576; Nov./Dec. 2011 (Year: 2011).*
The website downloaded Jan. 9, 2020 from https://international.neb.com/faqs/2015/04/10/what-is-the-difference-between-glycosylation-and-glycation; 1 page (Year: 2020).*
Machine translation of the specification of FR1311764; downloaded Jan. 10, 2020 (Year: 2020).*
Lowry et al., J. Clin. Path., 30, Suppl. (Ass. Clin. Path.), 7, 16-21 (Year: 1976).*
Brodsky et al., "Caprylic Acid Precipitation Method for Impurity Reduction: an Alternative to Conventional Chromatography for Monoclonal Antibody Purification", Biotechnology and Bioengineering, Wiley & Sons, Hoboken, NJ, vol. 109, No. 10 (Oct. 2012) pp. 2589-2598.
Johnston et al., "Low pH, Caprylate Incubation as a Second Viral Inactivation Step in the Manufacture of Albumin Parametric and Validation Studies", Biologicals, Academic Press Ltd., London GB, vol. 31, No. 3 (Sep. 2003) pp. 213-221.
Lundblad et al., "Inactivation of Lipid-Enveloped Viruses in Proteins by Caprylate", Vox Sanguinis, S. Karger AG, Basel CH, vol. 60, No. 2 (Jan. 1991) pp. 75-81.
Office Action issued in corresponding Colombian Application based on PCT/EP2016/064668.
Office Action dated Sep. 5, 2019 in corresponding Russian Application No. 2017145983/04(078655).
Search Report dated Sep. 5, 2019 in corresponding Russian Application No. 2017145983/04(078655).
Péjaudier et al., "Caprylic Acid as an Aid for the Rapid Isolation of Human Ceruloplasmin," Clinica Chimica Acta, 1970, 30(2), 387-394.

* cited by examiner

*Primary Examiner* — Christina M Borgeest
(74) *Attorney, Agent, or Firm* — Foley & Lardner LLP

(57) ABSTRACT

Methods of purification and/or viral deactivation of a protein (e.g. glycoprotein) comprising a step of treating the protein (e.g. glycoprotein) with a combination of caprylic acid and ethanol.

19 Claims, 3 Drawing Sheets

METHODS OF PURIFICATION AND/OR VIRAL INACTIVATION

CROSS-REFERENCE TO RELATED APPLICATIONS

Figure 1:
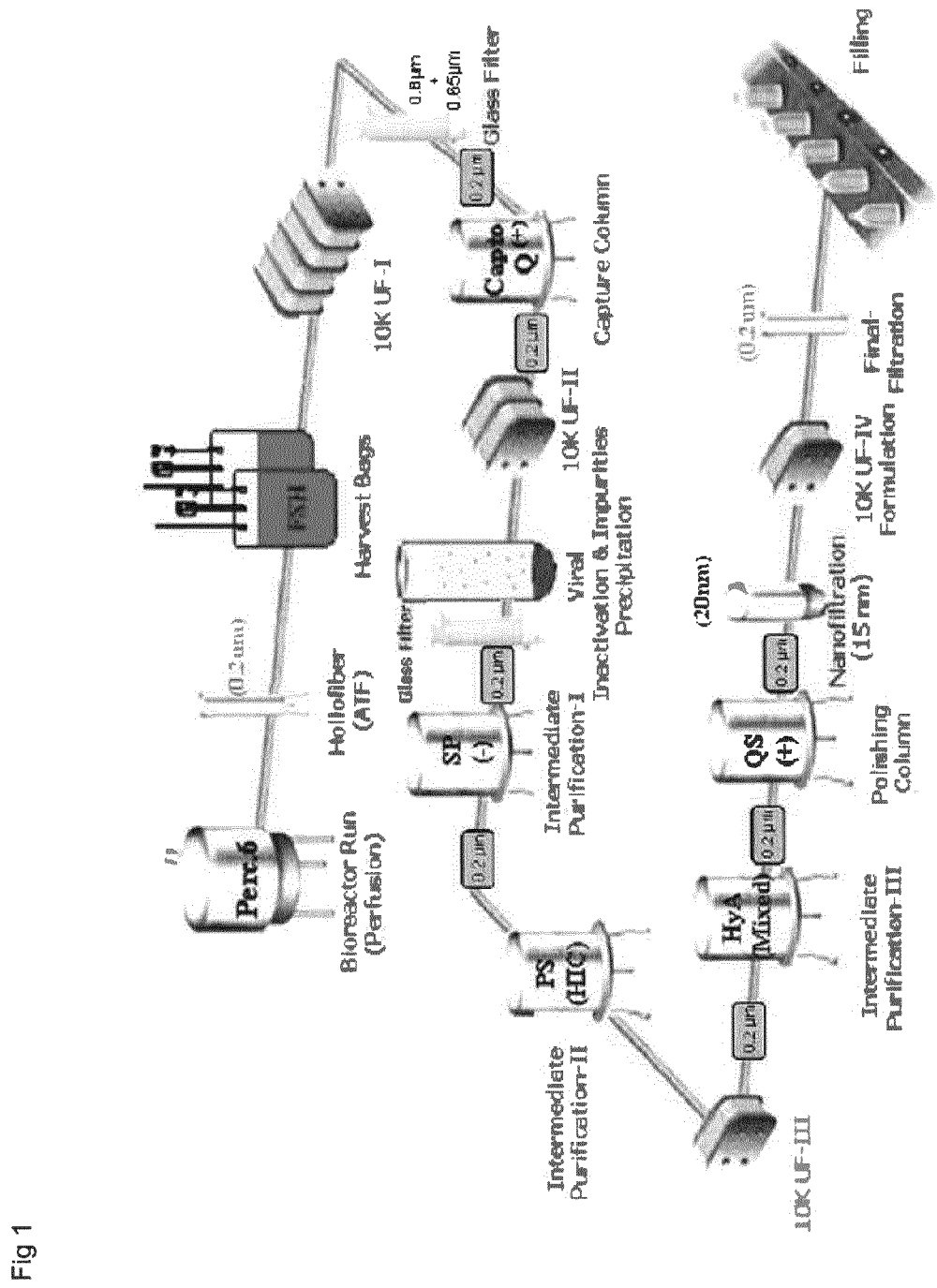

This application is the U.S. National Stage of International Application PCT/EP2016/064668, filed Jun. 24, 2016, which claims priority from European Patent Application No. 15174029.7, filed Jun. 26, 2015.

The present invention relates to methods of purification of proteins (or protein products) and/or methods of viral deactivation of proteins (or protein products). The present invention relates to methods of purification of glycoproteins (or glycoprotein products) and/or methods of viral deactivation of glycoproteins (or glycoprotein products). The proteins/glycoproteins may be, for example, recombinant glycoproteins such as FSH, hCG or LH, produced in host cells. The proteins/glycoproteins may be urinary derived.

Many glycoproteins are used in therapeutic treatments. For example, gonadotropins are a class of glycoproteins which are used in the treatment of infertility. The gonadotropins are a group of heterodimeric glycoprotein hormones which regulate gonadal function in the male and female. They include follicle stimulating hormone (FSH), luteinising hormone (LH) and chrorionic gonadotropin (CG).

FSH and hCG extracted from the urine of pregnant and postmenopausal women have been used for many years in infertility treatment. The production of FSH and hCG extracted from the urine involves the collection and processing of large amounts of urine.

As an alternative to urinary derived products, recombinant versions of FSH and hCG are available. The presently approved products (Gonal-F, Ovitrelle from Merck Serono; Puregon from MSD) are produced (expressed) in Chinese hamster ovary (CHO) cells.

The present applicants have developed a recombinant FSH and a recombinant hCG, both of which are expressed in a PER.C6® cell line. The PER.C6® cell line derived FSH product, and methods of its production, are disclosed in International patent application Nos. PCT/GB2009/000978 (published as WO2009/127826A), and PCT/EP2012/065507 (published as WO2013/020996). This product (FE999049) has completed Phase III clinical trials in Europe. The PER.C6® cell line derived recombinant hCG product, and a method of its production, are disclosed in PCT/GB2010/001854 (published as WO2011/042688).

The present applicants have developed techniques which may be used for purification of e.g. recombinant FSH and recombinant hCG produced in mammalian cell lines (e.g. the recombinant FSH disclosed in WO2009/127826A and WO2013/020996, and the recombinant hCG disclosed in WO2011/042688).

According to the present invention in a first aspect there is provided a method of purification of a protein [e.g. a glycoprotein, e.g. a recombinant glycoprotein, a (e.g. recombinant) gonadotropin, a (e.g. recombinant) FSH, hCG or LH], the method comprising a step of treating the protein [e.g. a glycoprotein, e.g. a recombinant glycoprotein, a (e.g. recombinant) gonadotropin, a (e.g. recombinant) FSH, hCG or LH] with a combination of caprylic acid and ethanol.

The method may comprise treating a solution of the protein [e.g. in water, buffer or other medium (for example a buffer; 100 mM ammonium acetate, 30-50 mM NaCl, pH 9-pH 9.5)] with a combination of caprylic acid and ethanol. The method may comprise treating a solution of the protein (e.g. glycoprotein) in a buffer (e.g. ammonium acetate buffer) at a pH 6.5 to 12, for example pH 7.5 to 10, for example pH 9 to 9.5.

The step of treating the glycoprotein with a combination of caprylic acid and ethanol may take place at acid pH, for example at pH 2 to pH 6.5, for example pH 3 to pH 6.5, for example pH 4 to pH 6 (for example pH 5.5±0.1) preferably pH 4.5 to pH 5.5]. The use of acidic condition (e.g. pH 4-pH 6) is due to caprylic acid activity. Caprylic acid can inactivate enveloped viruses by disrupting the virus membrane; this is enabled by the non-charged form of caprylic acid, which can penetrate the virus hydrophobic membrane. Caprylic acid is not charged at a pH which is close to its pKa (pH 4.9). At a ΔpH of 1 unit up (~pH 5.9), 100% of the caprylic molecules are negatively charged and thus less efficient for viral inactivation.

The protein may be a recombinant protein or a urinary derived protein. The protein may be a glycoprotein. The protein/glycoprotein may be a gonadotropin, for example FSH, hCG or LH. The glycoprotein may be a recombinant glycoprotein, e.g. a recombinant gonadotropin, e.g. recombinant FSH, hCG or LH. Preferably the protein/glycoprotein is a recombinant glycoprotein (e.g. recombinant gonadotropin, e.g. recombinant FSH, hCG or LH) produced in a cell (cell line) by a method comprising culturally the cell (cell line) in a suitable medium and harvesting the recombinant glycoprotein from said cell (cell line) and/or said medium (e.g. harvesting the recombinant protein from the cell culture supernatant). The cell (cell line) may be a mammalian cell (cell line), for example a CHO cell (line), a PER.C6® cell (line), a HEK293 cell (line), a HT1080 cell (line), a COS cell (line), a NOS cell (line), a SP20 cell (line), etc. Preferably the cell (cell line) is a PER.C6® cell (line).

Glycoproteins (gonadotropins, FSH, hCG, LH etc.), be they urinary or recombinant, are generally in the form of a solution/suspension in a medium. The glycoprotein may be present as a single isoform or as a mixture of isoforms, as is well known in the art. Herein the terms protein, glycoprotein, gonadotropin, FSH, hCG, LH etc. cover a solution or suspension comprising the protein, glycoprotein, gonadotropin, FSH, hCG, LH etc. Herein the terms protein, glycoprotein, gonadotropin, FSH, hCG, LH etc. cover a solution or suspension comprising the protein, glycoprotein, gonadotropin, FSH, hCG, LH etc., wherein the protein, glycoprotein, gonadotropin, FSH, hCG, LH etc. is present as a single isoform or as a mixture of isoforms. Thus, the term FSH covers a solution or suspension comprising FSH (e.g. wherein FSH is present as a single isoform or as a mixture of isoforms).

Herein, the phrase "treating the protein, (glycoprotein, gonadotropin, FSH, hCG, LH etc.) with a combination of caprylic acid and ethanol" means application of both caprylic acid and ethanol to the protein (glycoprotein, gonadotropin, FSH, hCG, LH etc.) such that the protein (glycoprotein, gonadotropin, FSH, hCG, LH etc.) is exposed to both caprylic acid and ethanol at the same time. Thus, this phrase covers techniques wherein caprylic acid and ethanol are added, either as a mixture, or as two separate reagents, to a solution of the protein (glycoprotein, gonadotropin, FSH, hCG, LH etc.), so the solution becomes a mixture of caprylic acid, ethanol and the protein (glycoprotein, gonadotropin, FSH, hCG, LH etc.); this phrase also covers other techniques where both caprylic acid and ethanol act on the protein (glycoprotein, gonadotropin, FSH, hCG, LH etc.) at the same time.

The applicants have surprisingly found that treating a solution containing recombinant protein/glycoprotein (e.g.

recombinant FSH, recombinant hCG) with ethanol and caprylic acid, for example a combination of 20 mM caprylic acid/30% ethanol, at acid pH, may lead to denaturing some viruses (causing their inactivation) and/or precipitation of other viruses and host cell proteins (impurities). The solution may then be centrifuged or filtered (to remove precipitated viruses and/or host cell proteins, e.g. using a depth filter such as a glass filter), such that the supernatant includes purified glycoprotein (e.g. recombinant FSH, recombinant hCG) for subsequent processing and use. The applicants have found that treatment of a solution containing recombinant glycoprotein (e.g. recombinant FSH, recombinant hCG) with ethanol and caprylic acid may (i) inactivate enveloped virus; and/or (ii) clear non-enveloped virus by precipitation (the precipitated virus may then be removed by a subsequent step of centrifugation or filtration by e.g. glass fibre filter); and/or (iii) remove host-related proteins by precipitation (the precipitated host-related proteins can then be removed by a subsequent step of centrifugation or filtration by e.g. glass fibre filter). This relatively simple treatment and filtration process provides a remarkable removal of impurities (64% to 79% of the host related impurities are removed in this process), with minimal loss of product glycoprotein (i.e. high yield).

The use of caprylic acid and ethanol (in e.g. purification/viral inactivation of recombinant FSH and/or recombinant hCG) has other advantages. Firstly, the combination of caprylic-acid and ethanol may shorten the purification process because the single step may have a dual function: viral inactivation and precipitation, as well as precipitation of host-cell proteins. Secondly, as described above, caprylic acid is most active with regard to viral inactivation at pH~4.9, but this low pH could theoretically damage the recombinant FSH product (by dissociation of the molecule, etc). According to the Henderson-Hasselbalch equation, at pH 5.5 approximately 20% of the CA is not charged, which provides a good balance of viral inactivation with reduced risk of damage to the recombinant FSH; the addition of EtOH (e.g. 30% EtOH) compensates the loss of caprylic acid activity in these conditions, which are less harmful to the protein. Finally, the combination of caprylic acid/EtOH allows the use of lower concentration of EtOH (e.g. 30%), which is extremely important in the manufacturing process, due to safety issues.

The caprylic acid concentration may be 10 mM to 30 mM caprylic acid, for example 18 mM to 25 mM caprylic acid, for example 19 mM to 23 mM caprylic acid, for example 20 mM caprylic acid. The EtOH may be 20% to 50% EtOH, for example 25% to 50% EtOH, for example 30% to 50% EtOH, for example 30% EtOH. The method may comprise a step of treating the glycoprotein with 30% to 50% ethanol and 18 mM to 25 mM caprylic acid, for example 20 mM caprylic acid and 30% ethanol.

The method may comprise treating the protein (glycoprotein) with ethanol and caprylic acid for 1 minute to 6 h incubation at a temperature 23±2° C. with stirring (e.g. for viral inactivation, with precipitation observed), for example treating the protein (glycoprotein) with ethanol and caprylic acid for 0.5 h to 1 h incubation at a temperature 23±2° C. with stirring (e.g. for viral inactivation, with precipitation observed). The method may comprise treating the protein (glycoprotein) with ethanol and caprylic acid at a temperature of 4°-8° C. for incubation of 1 minute to 32 h, without stirring (this step may continue/allow precipitation of host cell proteins (HCP) and non-enveloped viruses), for example treating the protein (glycoprotein) with ethanol and caprylic acid at a temperature of 4°-8° C. for incubation of 14 h to 16 h, without stirring (this step may continue/allow precipitation of HCP and non-enveloped viruses). In a preferred example the method comprises treating the protein (glycoprotein) with ethanol and caprylic acid for 0.5 h to 1 h incubation at a temperature 23±2° C. with stirring, followed by reduction to a temperature of 4°-8° C. and subsequent incubation for 16±2 hours, for example 14 h to 16 h, without stirring.

The method may comprise treating the protein (glycoprotein) with ethanol and caprylic acid for a duration of 1 h±10 min at a pH of 5.5±0.1 and a temperature of 23±2° C.

The method may comprise a further step of centrifuging or filtering the protein (glycoprotein) (solution) following treatment with caprylic acid and ethanol (e.g. through a depth filter, e.g. a glass fibre filter).

The method may comprise a further step of concentrating the protein (glycoprotein) (solution) to the desired concentration (of protein/glycoprotein) and/or other (e.g. subsequent) purification/formulation steps.

According to the present invention in a further aspect there is provided a method of viral inactivation in a protein [e.g. a glycoprotein, e.g. a recombinant glycoprotein, a (e.g. recombinant) gonadotropin, a (e.g. recombinant) FSH, hCG or LH)], the method comprising a step of treating the protein [e.g. a glycoprotein, e.g. a recombinant glycoprotein, a (e.g. recombinant) gonadotropin, a (e.g. recombinant) FSH, hCG or LH] with a combination of caprylic acid and ethanol.

The method may comprise treating a solution of the glycoprotein [e.g. in water, buffer or other medium (for example a buffer; 100 mM ammonium acetate, 30-50 mM NaCl, pH 9-pH 9.5)] with a combination of caprylic acid and ethanol. The method may comprise treating a solution of the protein (e.g. glycoprotein) in a buffer (e.g. ammonium acetate buffer) at a pH 6.5 to 12, for example pH 7.5 to 10, for example pH 9 to 9.5.

The step of treating the glycoprotein with a combination of caprylic acid and ethanol may take place at acid pH, for example at pH 2 to pH 6.5, for example pH 3 to pH 6.5, for example pH 4 to pH 6 (for example pH 5.5±0.1), preferably pH 4.5 to pH 5.5]. The use of acidic condition (e.g. pH 4-pH 6) is due to caprylic acid activity. Caprylic acid can inactivate enveloped viruses by disrupting the virus membrane; this is enabled by the non-charged form of caprylic acid, which can penetrate the virus hydrophobic membrane. Caprylic acid is not charged at a pH which is close to its pKa (pH 4.9). At a ΔpH of 1 unit up (~pH 5.9), 100% of the caprylic molecules are negatively charged and thus less efficient for viral inactivation.

The caprylic acid concentration may be 10 mM to 30 mM caprylic acid, for example 18 mM to 25 mM caprylic acid, for example 19 mM to 23 mM caprylic acid, for example 20 mM caprylic acid. The EtOH may be 20% to 50% EtOH, for example 25% to 50% EtOH, for example 30% to 50% EtOH, for example 30% EtOH. The method may comprise a step of treating the glycoprotein with 30% to 50% ethanol and 18 mM to 25 mM caprylic acid, for example 20 mM caprylic acid and 30% ethanol.

The method may comprise treating the protein (glycoprotein) with ethanol and caprylic acid for 1 minute to 6 h incubation at a temperature 23±2° C. with stirring, for example treating the protein (glycoprotein) with ethanol and caprylic acid for 0.5 h to 1 h incubation at a temperature 23±2° C. with stirring. The method may comprise treating the protein (glycoprotein) with ethanol and caprylic acid at a temperature of 4°-8° C. for incubation of 1 minute to 32 h, without stirring, for example treating the protein (glycoprotein) with ethanol and caprylic acid at a temperature of 4°-8° C. for incubation of 14 h to 16 h, without stirring. In a preferred example the method comprises treating the glycoprotein with ethanol and caprylic acid for 0.5 h to 1 h incubation at a temperature 23±2° C. with stirring, followed by reduction to a temperature of 4°-8° C. and subsequent incubation for 14 h to 16 h, without stirring.

The method may comprise treating the protein (glycoprotein) with ethanol and caprylic acid for a duration of 1 h±10 min at a pH of 5.5±0.1 and a temperature of 23±2° C.

The method may comprise a further step of centrifuging or filtering the protein (glycoprotein) (solution) following treatment with caprylic acid and ethanol (e.g. through a glass fibre filter). The method may comprise a further step of concentrating the protein (glycoprotein) (solution) to the desired concentration (of protein/glycoprotein) and/or other (e.g. subsequent) purification/formulation steps.

The protein may be a recombinant protein or a urinary derived protein. The protein may be a glycoprotein. The protein/glycoprotein may be a gonadotropin, for example FSH, hCG or LH. The protein/glycoprotein may be a recombinant glycoprotein, e.g. a recombinant gonadotropin, e.g. recombinant FSH, hCG or LH. Preferably the protein/glycoprotein is a recombinant glycoprotein (e.g. recombinant gonadotropin, e.g. recombinant FSH, hCG or LH) produced in a cell (cell line) by a method comprising culturally the cell (cell line) in a suitable medium and harvesting the recombinant glycoprotein from said cell (cell line) and/or said medium (e.g. harvesting the recombinant protein from the cell culture supernatant. The cell (cell line) may be a mammalian cell (cell line), for example a CHO cell (line), a PER.C6® cell (line), a HEK293 cell (line), a HT1080 cell (line), a COS cell (line), a NOS cell (line), a SP20 cell (line) etc. Preferably the cell (cell line) is a PER.C6® cell (line).

According to the present invention in a further aspect there is provided a protein which has been purified and or virally inactivated by a method described above. The protein may be a recombinant protein or a urinary derived protein. The protein may be a glycoprotein. The glycoprotein may be a recombinant glycoprotein, e.g. a recombinant gonadotropin, e.g. recombinant FSH, hCG or LH. Preferably the glycoprotein is a recombinant glycoprotein (e.g. recombinant gonadotropin, e.g. recombinant FSH, hCG or LH) produced in a cell (cell line) by a method comprising culturally the cell (cell line) in a suitable medium and harvesting the recombinant glycoprotein from said cell (cell line) and/or said medium (e.g. harvesting the recombinant protein from the cell culture supernatant). The cell (cell line) may be a mammalian cell (cell line), for example a CHO cell (line), a PER.C6® cell (line), a HEK293 cell (line), a HT1080 cell (line), a COS cell (line), a NOS cell (line), a SP20 cell (line) etc. Preferably the cell (cell line) is a PER.C6® cell (line).

According to the present invention in a further aspect there is provided a pharmaceutical composition [e.g. for (use in) the treatment of infertility] comprising a protein (e.g. a glycoprotein, e.g. a recombinant glycoprotein, e.g. recombinant FSH, recombinant hCG) which has been purified and or virally inactivated by a method described above.

According to the present invention in a further aspect there is provided a method of treatment (e.g. of infertility) comprising a step of administration to a patient in need thereof a pharmaceutical composition comprising a protein (e.g. a glycoprotein, e.g. a recombinant glycoprotein, e.g. recombinant FSH, recombinant hCG) which has been purified and or virally inactivated by a method described above.

The treatment of infertility may comprise assisted reproductive technologies (ART), ovulation induction or intrauterine insemination (IUI). The pharmaceutical composition may be used, for example, in medical indications where known FSH, LH, hCG preparations are used.

The product or composition can be formulated into well-known compositions for any route of drug administration, e.g. oral, rectal, parenteral, transdermal (e.g. patch technology), intravenous, intramuscular, subcutaneous, intracisternal, intravaginal, intraperitoneal, local (powders, ointments or drops) or as a buccal or nasal spray. A typical composition comprises a pharmaceutically acceptable carrier, such as aqueous solution, non toxic excipients, including salts and preservatives, buffers and the like, as described in Remington's Pharmaceutical Sciences fifteenth edition (Matt Publishing Company, 1975), at pages 1405 to 1412 and 1461-87, and the national formulary XIV fourteenth edition (American Pharmaceutical Association, 1975), among others.

Examples of suitable aqueous and non-aqueous pharmaceutical carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. The compositions of the present invention also can contain additives such as but not limited to preservatives, wetting agents, emulsifying agents, surfactants and dispersing agents. Antibacterial and antifungal agents can be included to prevent growth of microbes and includes, for example, m-cresol, benzyl alcohol, paraben, chlorobutanol, phenol, sorbic acid, and the like. If a preservative is included, benzyl alcohol, phenol and/or m-cresol are preferred; however, the preservative is by no means limited to these examples. Furthermore, it may be desirable to include isotonic agents such as sugars, sodium chloride, and the like. The product or composition may further comprise a salt comprising a pharmaceutically acceptable alkali metal cation selected from the group consisting of $Na^+$— or $K^+$— salts, or a combination thereof. Preferably the salt is a Na+— salt, for example NaCl or $Na_2SO_4$.

Preferably the product or composition comprises a glycoprotein and one or more of Polysorbate 20, L-methionine, phenol, disodium sulphate and sodium phosphate buffer, sucrose and citrate buffers.

Injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use. Injectable formulations can be supplied in any suitable container, e.g. vial, pre-filled syringe, injection cartridges, and the like.

The composition may be formulated for single use or for multiple use (multiple dose). If the product or composition is formulated for multiple use, it is preferred that a preservative is included. If a preservative is included, benzyl alcohol, phenol and/or m-cresol are preferred; however, the preservative is by no means limited to these examples. The single use or multiple use formulated product or composition may further comprise a salt comprising a pharmaceutically acceptable alkali metal cation selected from the group consisting of $Na^+$— or $K^+$— salts, or a combination thereof. Preferably the salt is a Na+— salt, for example NaCl or $Na_2SO_4$.

The product or composition may be included in a container such as a vial, prefilled cartridge (e.g. for single administration or multiple use) or an injection device such as a "pen" for e.g. administration of multiple doses.

The vials may be packaged in a blister package or other means to maintain sterility. Any product can optionally contain instructions for using the FSH (and e.g. hCG if present) formulations. The pH and exact concentration of the various components of the pharmaceutical composition are adjusted in accordance with routine practice in this field. See GOODMAN and GILMAN's THE PHARMACOLOGICAL BASIS FOR THERAPEUTICES, $7^{th}$ ed. In a preferred embodiment, the compositions of the invention are supplied as compositions for parenteral administration. General methods for the preparation of the parenteral formulations are known in the art and are described in REMINGTON; THE SCIENCE AND PRACTICE OF PHARMACY, supra, at pages 780-820. The parenteral compositions can be supplied in liquid formulation or as a solid which will be mixed with a sterile injectable medium just prior to administration. In an especially preferred embodiment, the parenteral compositions are supplied in dosage unit form for ease of administration and uniformity of dosage.

Figure 2:
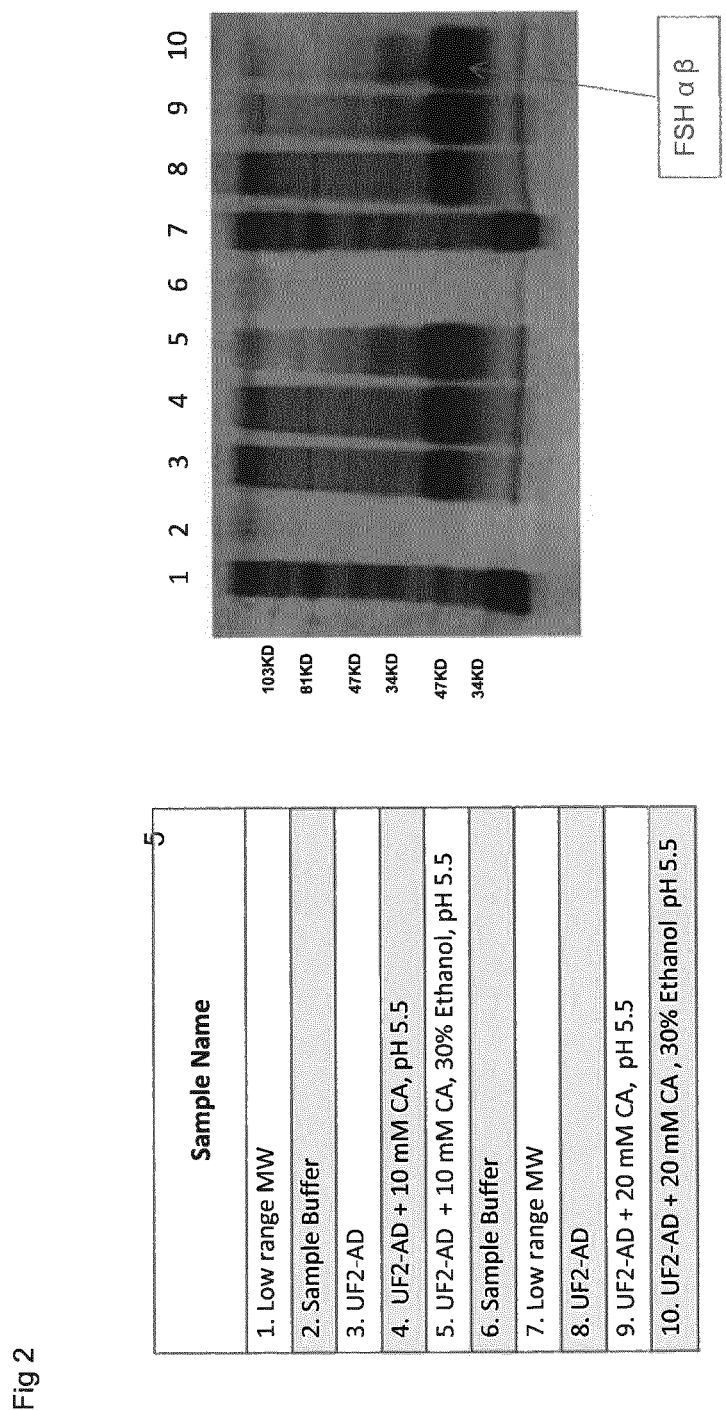
Figure 3:
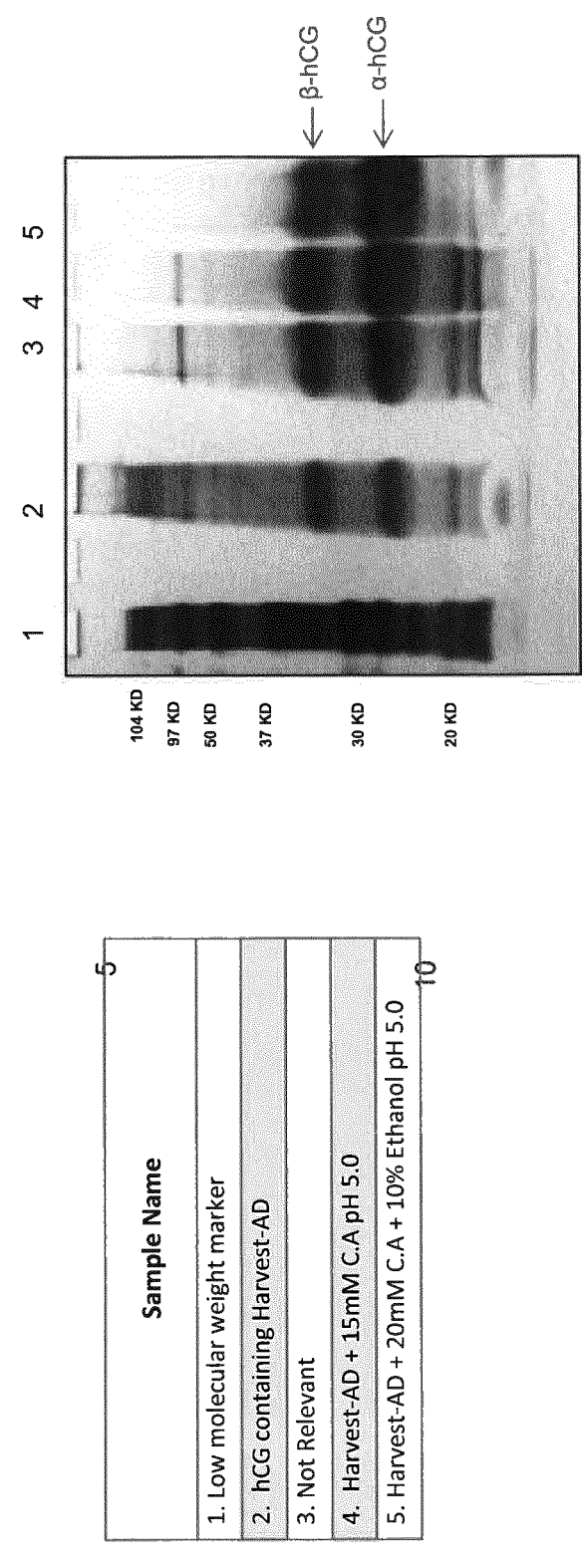

The present invention will now be described with reference to the attached drawings in which:

FIG. 1 shows a scheme of the recombinant FSH purification (viral deactivation) process according to an embodiment of the present invention;

FIG. 2 shows the gel pattern following qualitative estimation of the impurities removal for various treated UF2-AD (Ultrafiltration after dialysis) FSH samples run on 12% reduced PAGE (polyacrylamide gel electrophoresis), wherein lane 1 LMW (low molecular weight) markers, lane 2 is Sample Buffer, lane 3 is UF2-AD, lane 4 is UF2-AD+10 mM CA, pH 5.5, lane 5 is UF2-AD+10 mM CA, 30% Ethanol, pH 5.5, lane 6 is Sample Buffer, lane 7 is low range MW, lane 8 is UF2-AD, lane 9 is UF2-AD+20 mM CA, pH 5.5 and lane 10 is UF2-AD+20 mM CA, 30% Ethanol pH 5.5 (see Example 3); and FIG. 3 shows the gel pattern following qualitative estimation of the impurities removal for various treated hCG samples run on 12% reduced PAGE (polyacrylamide gel electrophoresis), wherein lane 1 is LMW (low molecular weight) markers, lane 2 is hCG containing Harvest-AD, lane 3 is NR—Not Relevant, lane 4 is supernatant of [Harvest-AD+15 mM C.A pH 5.0], and lane 5 is supernatant of [Harvest-AD+20 mM C.A+10% Ethanol pH 5.0], see Example 4.

EXAMPLE 1

FIG. 1 shows an overview of the whole recombinant FSH purification process. As can be seen in FIG. 1, recombinant FSH is expressed in a PER.C6® cell line engineered by the methods disclosed in WO2013/020996 and WO2009/127826A using a bioreactor.

The bioreactor is seeded and cell growth promoted by methods known to those skilled in the art, and the bioreactor run in perfusion mode to produce and continuously harvest recombinant FSH, using a Hollofibre (ATF4) system available from Repligen. The seeding of at least $1\times10^6$ cells/mL in a total volume of 4±1 Litre takes place in 6GRO medium. The production takes place in the ProPer-1 medium, and the bioreactor harvest is collected into polyethylene bags. Thus, in this example the protein (glycoprotein) is a recombinant glycoprotein (recombinant FSH) produced in a PER.C6® cell line by a method comprising culturally the cell line in a suitable medium (ProPer-1 medium) and harvesting the recombinant glycoprotein from the medium (by harvesting the recombinant protein from the cell culture supernatant).

The bioreactor harvest is pooled and subjected to 10 kDa ultrafiltration/diafiltration step (UF1) which, reduces the concentration of the harvest, conditions the harvest (in terms of pH and conductivity) for Capto-Q chromatography, and removes pigments and low molecular weight components of the culture medium. The retentate is filtered through a glass fibre filter of 0.8+0.65 µm to clarify the process solution (see FIG. 1), and subsequently subjected to 0.2 µm filtration as a bioburden control. Capto-Q anion exchange chromatography is then used, by methods well known in the art, to capture the recombinant FSH, and to remove DNA, endotoxin, host cell proteins and process related impurities. A further 0.2 µm filtration is performed as a bioburden control.

The filtered Capto-Q eluate is subjected to a further 10 kDa ultrafiltration/diafiltration (UF2) with the purpose of desalting and volume reduction prior to purification/viral inactivation, by methods well known in the art.

CA/EtOH Step

The retentate of UF2 is a solution of recombinant FSH in a buffer (100 mM ammonium acetate, 30 mM NaCl, pH 9.3-pH 9.7). The pH of the protein solution is first reduced from pH 9.3-pH 9.7 to pH 6.3±0.3 at 23±2° C. with stirring, then treated with a combination of 20 mM caprylic acid/30% ethanol (CA/EtOH) followed by further adjustment of the pH to 4.5-5.6 (the pH is adjusted by 1 M HCl). After this treatment the protein solution remains for 0.5 h to 1 h incubation at 23±2° with stirring (during this time viral inactivation takes place and white precipitation flakes-like are observed). At the end of 0.5 h-1 h, the temperature of the protein solution is reduced to 4°-8° C., and the solution incubated for a further 14 h to 18 h, e.g. 14 to 16 h, without stirring (this allows the precipitation of HCP and non-enveloped viruses to continue). The CA/ETOH treatment step has a triple activity: (i) inactivation of enveloped virus; (ii) clearance of non-enveloped virus by precipitation followed by clarification step aimed to remove the precipitate; and (iii) host-related protein removal by precipitation.

The precipitated impurities (non enveloped virus and host related protein) are removed by a step of filtration through a glass fibre filter of 0.8+0.65 micrometres, a filtration step which also clarifies the recombinant FSH solution.

A further 0.2 µm filtration is performed as a bioburden control.

The solution is then subject to Sulfopropyl-Sepharose cation-exchange chromatography (SP-FF) by methods well known in the art to remove the caprylic acid, ethanol and further host cell proteins. A further 0.2 µm filtration is performed as a bioburden control, followed by additional step of purification using Phenyl-Sepharose hydrophobic interaction chromatography (PS-FF) to remove free recombinant FSH sub units and host cell proteins.

The PS eluate is subjected to a third 10 kDa ultrafiltration/diafiltration step (UF3) to remove the salt and condition the solution for the next step. A further 0.2 µm filtration is performed as a bioburden control, prior to hydroxyapatite adsorption chromatography (HyA), aimed to remove dissociated FSH sub units and basic heterodimers, followed by a further 0.2 µm filtration performed as a bioburden control.

A Q-sepharose anion-exchange chromatography (QS-FF) "polishing step" is performed in bind/elute mode to remove host proteins, DNA, endotoxins and potential viruses. A further bioburden control 0.2 µm filtration then takes place, prior to pooling of QS MPs and nanofiltration to remove potential viruses. The supernatant is subjected to a fourth 10 kDa ultrafiltration/diafiltration step (UF4) to concentrate the recombinant FSH to 0.5 to 1.1 mg/ml, followed by the addition of polysorbate 20 to final concentration of 0.005 mg/ml. These are dialysis and buffer adjustment steps, which are well known in the art. The recombinant FSH is subject to a final 0.2 μm filtration step prior to aliquoting into primary packaging and storing at −20° C. until shipment.

The applicants have found that the treatment with caprylic acid/ethanol is capable of markedly reducing the host-related impurities. According to various manufacturing runs (data not shown) 64 to 79% of the host related impurities are removed by the CA/EtOH step (and subsequent glass fibre filtration) described above, while a high yield of approximately 90 to 95% of the FSH was recovered. This is a significant reduction in host-related impurities which is provided by a simple process, with minimal loss of product protein (product glycoprotein).

The remarkable viral clearance efficiency of the this step is summarized in Table 1, which shows a summary of the $\log_{10}$ reduction factors, which are in the region of ≥4.25 to ≥5.41. A log-reduction factor (LRF)≥4 $\log_{10}$ (e.g. up to 8 $\log_{10}$ or greater) is generally considered high, robust and effective.

TABLE 1

Summary of the $\log_{10}$ reduction factors (rFSH)

| Process Step | Study number | Enveloped Viruses | | Nonenveloped Virus |
|---|---|---|---|---|
| | | MuLV | PRV | EMCV[1] |
| Caprylic acid/Ethanol treatment (protein conc. 2 mg/mL) | K1/B28/12 K1/B28/13[1] | ≥4.88/≥5.12 | ≥5.29/≥5.41 | ≥4.42/≥4.47 |
| Caprylic acid/Ethanol treatment (protein conc. 6 mg/mL) | K1/B28/12 K1/B28/13[1] | ≥4.94/≥4.58 | ≥5.11/≥5.29 | ≥4.25/≥4.36 |

[1]Study with EMCV contains glass fiber filtration after the treatment

The Example above relates to rFSH, but those skilled in the art will appreciate that process [e.g. the CA/EtOH step (and subsequent glass fibre filtration)] described above is readily applicable to purification/viral inactivation of other proteins (e.g. glycoproteins), for example rhCG [e.g. rhCG produced in a PER.C6® cell line by the method of in PCT/GB2010/001854 (published as WO2011/042688)].

EXAMPLE 2

In another example of a method of the invention, there is provided an hCG purification/viral inactivation process. A method similar to Example 1 above (minus the Sulfopropyl-Sepharose cation-exchange chromatography (SP-FF) step) was used for purification/viral inactivation of rhCG produced in a PER.C6 cell line by the method of in PCT/GB2010/001854 (published as WO2011/042688). The applicants found that chemical inactivation by caprylic acid and ethanol at acidic pH, i.e. using the CA/EtOH step described in Example 1, removed approximately 65% of non hCG impurities (by precipitation), while a high yield of approximately 90% of the hCG was recovered.

The excellent viral clearance efficiency of the CA/EtOH step in the Example is summarized in Table 2. Viral inactivation of MuLV was effective as determined by the high LRF obtained, in a range ≥5.31 to ≥5.48. LRFs between ≥2.03 and ≥2.74 were obtained for the CA/EtOH treatment and precipitate removal.

TABLE 2

Summary of the $\log_{10}$ reduction factors (rhCG)

| | | LRFs | |
|---|---|---|---|
| Process Step | Study Number | Enveloped Virus (MuLV) | Nonenveloped Virus (PPV) |
| Caprylic acid/Ethanol treatment (protein conc. 2 mg/mL) | KOP1-B01-15 | ≥5.43/≥5.31 | ≥2.03/≥2.21 |
| Caprylic acid/Ethanol treatment (protein conc. 6 mg/mL) | KOP1-B01-15 | ≥5.31/≥5.48 | ≥2.68/≥2.74 |

EXAMPLE 3: EVALUATION OF PRECIPITATION CONDITIONS FOR IMPURITIES REMOVAL IN RFSH-CONTAINING SOLUTION

Experiment Description:

The UF2-AD (Ultrafiltration after dialysis) intermediate obtained using the rFSH purification process of Example 1 (up to the CA/EtOH step) contained 100 mM Ammonium Acetate+30 mM NaCl pH 9.50±0.20, 11.00±0.50 mS/cm. This was aliquoted and each aliquot was subjected to different precipitation conditions for impurities removal (rFSH is soluble in the solution). The tested precipitation conditions are as follows:

1. UF2-AD without treatment (control)
2. UF2-AD+10 mM Caprylic acid (CA), pH 5.5
3. UF2-AD+10 mM CA, 30% Ethanol, pH 5.5
4. UF2-AD+20 mM CA, pH 5.5
5. UF2-AD+20 mM CA, 30% Ethanol, pH 5.5

All treated samples were incubated for 30 min at RT with stirring followed by additional incubation of 30 min without stirring. Further incubation was performed at 2-8° C. for 16-20 hr. The generated precipitants were removed by centrifugation while supernatants were collected.

Performance Parameters of the Precipitation Process:
rFSH Recovery rFSH concentration in all the samples were determined by FSH ELISA and the yields of each sample after treatment were calculated and are set out in Table 3.

As seen in Table 3, 96%, 106%, 106% and 98% of the rFSH in the UF2-ADs process solutions was recovered following precipitation with 10 mM CA, 10 mM CA+30% Ethanol, 20 mM CA and 20 mM CA+30% Ethanol, respectively. This indicates that the rFSH is not precipitated and stays soluble in solution.

Impurities Removal

The absorbance at 280 nm in the un-treated UF2-AD and in each of the supernatants of the treated UF2-ADs was measured and impurities removal was calculated, as set out in Table 3. 33.9%, 64.9%, 65.9% and 68.8% of the total $A_{280}$ impurity in the UF2-AD was removed after precipitation with 10 mM CA, 10 mM CA+30% Ethanol, 20 mM CA and 20 mM CA+30% Ethanol, respectively.

The un-treated UF2-AD and the supernatants of the various treated UF2-ADs were run on 12% reduced PAGE (polyacrylamide gel electrophoresis) for qualitative estimation of the impurities removal. The gel pattern is shown in FIG. 2. The supernatant obtained following precipitation by 10 mM CA+30% Ethanol (lane 5) and 20 mM CA+30% Ethanol pH 5.5 (lane 10) is substantially purer relative to the supernatant obtained following precipitation by 10 mM CA pH 5.5 (lane 4) and 20 mM CA (lane 9), respectively. This shows the synergistic effect of the addition of ethanol to Caprylic acid in the precipitation step.

Experiment Conclusions:

1. Precipitation of UF2-AD by Ethanol and Caprylic acid resulted in purer product compared to that obtained using Caprylic acid only.

2. The combination of Ethanol and Caprylic acid does not precipitate rFSH which stays soluble in solution, meaning this is a high yield purification and viral inactivation step.

impurities (while hCG is soluble in the solution). The tested precipitation conditions are as follows (Table 4):

1. Harvest-AD without treatment as a control;
2. Harvest-AD+15 mM CA, pH 5.0
3. Harvest-AD+20 mM CA, pH 5.0
4. Harvest-AD+20 mM CA+10% Ethanol, pH 5.0.

All treated samples were incubated for 1 hr at R.T with stirring. The generated precipitants were removed by centrifugation while supernatants were collected.

Performance Parameters of the Precipitation Process:

hCG Recovery

The hCG concentration in the un-treated harvest and in each of the supernatants of the treated Harvest ADs were determined and recoveries were calculated as detailed in Table 4.

Impurities Removal

The absorbance at 280 nm ($A_{280}$) in the un-treated harvest and in each of the supernatants of the treated Harvest ADs were determined and impurities removals were calculated as detailed in Table 4.

The un-treated harvest and the supernatants of the various treated Harvest ADs were run on 12% reduced PAGE (polyacrylamide gel electrophoresis) for qualitative estimation of the impurities removal. The gel pattern is shown in FIG. 3.

Discussion:

1. hCG Recovery—91%, 86% and 83% of the hCG in the Harvest-AD were recovered after precipitation with 15 mM CA, 20 mM CA and 20 mM CA+10% Ethanol respectively.

TABLE 3

Results Obtained from Different Precipitation Conditions for Impurities Removal in intermediate rFSH solution

| Supernatant of | Absorbance at 280 nm | | | rFSH (by ELISA) | | |
| --- | --- | --- | --- | --- | --- | --- |
| | $A_{280}$ | total $A_{280}$ | Removal (%) | μg/ml | total μg | Recov (%) |
| 1. UF2-AD | 3.265 | 32.650 | — | 677 | 6,770 | — |
| 2. UF2-AD + 10 mM CA, pH 5.5 | 2.066 | 21.571 | 33.9 | 207.1 | 6,487 | 96 |
| 3. UF2-AD + 10 mM CA, 30% Ethanol, pH 5.5 | 0.760 | 11.457 | 64.9 | 158.6 | 7,173 | 106 |
| 4. UF2-AD + 20 mM CA, pH 5.5 | 1.060 | 11.122 | 65.9 | 227.80 | 7,170 | 106 |
| 5. UF2-AD + 20 mM CA, 30% Ethanol pH 5.5 | 0.678 | 10.197 | 68.8 | 146.5 | 6,610 | 98 |

EXAMPLE 4: EVALUATION OF PRECIPITATION CONDITIONS FOR REMOVAL OF IMPURITIES IN HCG-CONTAINING HARVEST

Experiment Description:

hCG-containing harvest was concentrated ~40 fold and dialyzed with 100 mM glycine, 50 mM NaCl pH 9.0, 6 mS/cm buffer by 10 kDa ultrafiltration (UF) system. At the end of the UF, the recovered protein solution, Harvest-AD (After dialysis) material, was aliquoted and each aliquot was subjected to different precipitation conditions for removal of 2. Impurities Removal by $A_{280}$—56.6%, 55.8% and 63.0% of the total $A_{280}$ in the Harvest-AD were removed after precipitation with 15 mM CA, 20 mM CA and 20 mM CA+10% Ethanol respectively.

3. Impurities Removal by gel—the supernatant obtained following precipitation by 20 mM CA+10% Ethanol pH 5.0 (lane 5) is substantially purer relative to the supernatant obtained following precipitation by 15 mM CA pH 5.0 (lane 4)

Conclusions:

1. Precipitation of hCG-containing Harvest added with Ethanol and Caprylic acid resulted in a purer product compared to that obtained using only Caprylic acid.

TABLE 4

Results Obtained from Different Precipitation Conditions for Impurities Removal in hCG Containing Harvest

| | Absorbance at 280 nm | | | rFSH (by ELISA) | | |
|---|---|---|---|---|---|---|
| Supernatant of | $A_{280}$ | total $A_{280}$ | Removal (%) | µg/ml | total µg | Recov (%) |
| 1. Harvest AD | 4.295 | 107.375 | — | 757.14 | 18,929 | — |
| 2. Harvest AD + 15 mM CA, pH 5.0 | 1.738 | 46.578 | 56.6% | 639.72 | 17,144 | 91% |
| 3. Harvest AD + 20 mM CA, pH 5.0 | 1.792 | 47.488 | 55.8% | 612.24 | 16,224 | 86% |
| 4. Harvest AD + 20 mM CA, 10% Ethanol, pH 5.0 | 1.369 | 39.701 | 63.0% | 543.8 | 15,770 | 83% |

The invention claimed is:

1. A method of purification of a glycoprotein, the method comprising a step of treating the glycoprotein with a combination of caprylic acid and ethanol, wherein the glycoprotein is FSH, hCG, or LH.

2. A method according to claim 1, which comprises treating a solution of the glycoprotein with a combination of caprylic acid and ethanol.

3. A method according to claim 2, further comprising concentrating the glycoprotein solution.

4. A method according to claim 1, wherein the glycoprotein is recombinant FSH, hCG, or LH.

5. A method according to claim 1, wherein the glycoprotein is a recombinant FSH, hCG, or LH produced in a cell by a method comprising culturing the cell in a suitable medium and harvesting the recombinant FSH, hCG, or LH from said cell and/or said medium.

6. A method according to claim 5, wherein the cell is a mammalian cell.

7. A method according to claim 1, wherein treating the glycoprotein with a combination of caprylic acid and ethanol takes place at pH 2 to pH 6.5.

8. A method according to claim 7, wherein treating the glycoprotein with a combination of caprylic acid and ethanol takes place at pH 3 to pH 6.5.

9. A method according to claim 7, wherein treating the glycoprotein with a combination of caprylic acid and ethanol takes place at pH 4 to pH 6.

10. A method according to claim 7, wherein treating the glycoprotein with a combination of caprylic acid and ethanol takes place at pH 4.5 to pH 5.5.

11. A method according to claim 1, wherein the caprylic acid concentration is from 10 mM to 30 mM caprylic acid.

12. A method according to claim 1 which comprises treating the glycoprotein with ethanol and caprylic acid for an incubation time of from 1 minute to 6 hours at a temperature of 23±2° C. with stirring.

13. A method according to claim 1, further comprising filtering the glycoprotein following the treatment with caprylic acid and ethanol.

14. A method according to claim 13, wherein the glycoprotein is filtered using a glass fiber filter.

15. A method according to claim 1, wherein the ethanol concentration is from 20% to 50% (v/v).

16. A method according to claim 1 which comprises treating the glycoprotein with ethanol and caprylic acid at a temperature of 4°-8° C. for an incubation time of from 1 minute to 32 hours, without stirring.

17. A method according to claim 1 which comprises treating the glycoprotein with ethanol and caprylic acid for an incubation time of from 0.5 hours to 1 hour at a temperature of 23±2° C. with stirring, followed by reducing the temperature to a temperature of 4°-8° C. and subsequent incubation a temperature of 4°-8° C. for 14 hours to 18 hours, without stirring.

18. A method according to claim 1 which comprises treating the glycoprotein with ethanol and caprylic acid for a duration of 1 hour±10 minutes at a pH of 5.5±0.1 and a temperature of 23±2° C.

19. A method of viral inactivation in a glycoprotein, the method comprising a step of treating the glycoprotein with a combination of caprylic acid and ethanol, wherein the glycoprotein is FSH, hCG, or LH.

\* \* \* \* \*